(12) United States Patent
Ozawa et al.

(10) Patent No.: US 7,588,757 B2
(45) Date of Patent: Sep. 15, 2009

(54) METHODS OF TREATING PARKINSON'S DISEASE USING RECOMBINANT ADENO-ASSOCIATED VIRUS VIRIONS

(75) Inventors: Keiya Ozawa, Kawachi-gun (JP); Ken-ichi Fujimoto, Kawachi-gun (JP); Shin-ichi Muramatsu, Minamikawachi-machi (JP); Kunihiko Ikeguchi, Minamikawachi-machi (JP); Imaharu Nakano, Saitama (JP)

(73) Assignee: Genzyme Corporation, Cambridge, MA (US)

( * ) Notice: Subject to any disclaimer, the term of this patent is extended or adjusted under 35 U.S.C. 154(b) by 767 days.

(21) Appl. No.: 10/096,723

(22) Filed: Mar. 13, 2002

(65) Prior Publication Data

US 2002/0172664 A1 Nov. 21, 2002

Related U.S. Application Data

(60) Provisional application No. 60/275,903, filed on Mar. 14, 2001.

(51) Int. Cl.
| | |
|---|---|
| *A01N 63/00* | (2006.01) |
| *A01N 65/00* | (2006.01) |
| *A01N 43/04* | (2006.01) |
| *A61K 48/00* | (2006.01) |
| *A61K 31/70* | (2006.01) |

(52) U.S. Cl. .................. 424/93.2; 424/93.1; 514/14
(58) Field of Classification Search ............ 424/93.1, 424/93.2, 93.6; 514/44
See application file for complete search history.

(56) References Cited

U.S. PATENT DOCUMENTS

| | | | | |
|---|---|---|---|---|
| 6,103,226 A | * | 8/2000 | Kang et al. | 424/93.21 |
| 6,180,613 B1 | | 1/2001 | Kaplitt et al. | 514/44 |
| 6,309,634 B1 | | 10/2001 | Bankiewicz et al. | 424/93.2 |
| 6,506,378 B1 | * | 1/2003 | Kang | 424/93.21 |
| 2004/0013648 A1 | * | 1/2004 | Kingsman et al. | 424/93.2 |

OTHER PUBLICATIONS

Shen et al. (Jul. 20, 2000) Triple transduction with adeno-associated virus vectors expressing tyrosine hydroxylase, aromatic-L amino-acid decarboxylase, and GTP cyclohydrolase I for gene therapy of Parkinson's disease. Human Gene Therapy 11: 1509-1519.*
Thomas et al. (2003) Progress and problems with the use of viral vectors for gene therapy. Nature 4: 346-358.*
During et al., "In vivo expression of therapeutic human genes for dopamine production in the caudates of MPTP-treated monkeys using an AAV vector", *Gene Therapy* 5:820-827, 1998, Stockton Press.
Fan et al., "Behavioral Recovery in 6-Hydroxydopamine-Lesioned Rats by Cotransduction of Striatum with Tyrosine Hydroxylase and Aromatic L-Amino Acid Decarboxylase Genes Using Two Separate Adeno-Associated Virus Vectors", *Human Gene Therapy* 9:2527-2535, Nov. 20, 1998, Mary Ann Liebert, Inc.
Mandel et al., Characterization of Intrastriatal Recombinant Adeno-Associated Virus-Mediated Gene Transfer of Human Tyrosine Hydroxylase and Human GTP-Cyclohydrolase I in a Rat Model of Parkinson's Disease, *The Journal of Neuroscience* 18(11):4271-4284, Jun. 1, 1998.
Kaplitt et al., "Long-term gene expression and phenotypic correction using adeno-associated virus vectors in the mammalian brain", *Nature Genetics* 8:148:154, Oct. 1994.
Stephen R. Wachtel et al., *Role of Aromatic L-Amino Acid Decarboxylase for Dopamine Replacement by Genetically Modified Fibroblasts in a Rat Model of Parkinson's Disease*, Journal of Neurochemistry, pp. 2055-2063 (1997).

* cited by examiner

*Primary Examiner*—Anne-Marie Falk

(57) ABSTRACT

Methods for treating Parkinson's disease (PD) are provided. Recombinant adeno-associated virus (rAAV) virions are used to deliver genes encoding dopamine-synthesizing enzymes to the central nervous system of a primate. Once delivered, the genes are expressed, which then results in dopamine synthesis and amelioration in the clinical signs and symptoms of PD. The methods of the present invention can be used to deliver the three central dopamine synthesizing enzymes: tyrosine hydroxylase, aromatic L-amino acid decarboxylase, and guanosine triphosphate cyclohydrolase I thereby enhancing dopamine biosynthesis and providing for enhanced therapeutic efficacy.

3 Claims, 2 Drawing Sheets

SEQUENCE LISTING

<160> NUMBER OF SEQ ID NOS: 9

<210> SEQ ID NO 1
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 1
gctcggtacc cgggcggagg ggtggagtcg                                    30

<210> SEQ ID NO 2
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 2
taatcattaa ctacagcccg gggatcctct                                    30

<210> SEQ ID NO 3
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 3
ggtttgaacg agcgctcgcc atgc                                          24

<210> SEQ ID NO 4
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 4
cgcgccgata tcgttaacgc ccgggcgttt aaacagcgct gg                      42

<210> SEQ ID NO 5
<211> LENGTH: 42
<212> TYPE: DNA

-continued

```
<213> ORGANISM: Artificial Sequence
<220> FEATURE:
<223> OTHER INFORMATION: synthetic oligonucleotide

<400> SEQUENCE: 5
cgcgccagcg ctgtttaaac gcccgggcgt taacgatatc gg                          42

<210> SEQ ID NO 6
<211> LENGTH: 7
<212> TYPE: DNA
<213> ORGANISM: adeno-associated virus 2

<400> SEQUENCE: 6 tatttaa                                                                  7

<210> SEQ ID NO 7
<211> LENGTH: 7
<212> TYPE: DNA
<213> ORGANISM: Artificial Sequence
<220> FEATURE:
<223> OTHER INFORMATION: synthetic sequence

<400> SEQUENCE: 7 ggggggg                                                                  7

<210> SEQ ID NO 8
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 8
tgtggtcacg ctgggggggg gggcccgagt gagcacg                                37

<210> SEQ ID NO 9
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 9
gtcgacaaat ctagatatcg cccgggcgga tcc                                    33
```

METHODS OF TREATING PARKINSON'S DISEASE USING RECOMBINANT ADENO-ASSOCIATED VIRUS VIRIONS

CROSS-REFERENCE TO RELATED APPLICATIONS

This application is related to provisional patent application Ser. No. 60/275,903, filed Mar. 14, 2001, now abandoned, entitled "Behavioral Recovery in a Primate Model of Parkinson's Disease by Triple Transduction of Striatal Cells with AAV Vectors Expressing Dopamine-Synthesizing Enzymes" from which application priority is claimed under 35 USC §119(e)(1).

FIELD OF THE INVENTION

The present invention relates generally to efficient delivery of viral vectors to the CNS. More particularly, the present invention relates to gene therapy for the treatment of central nervous system disorders, particularly those disorders that involve the neurotransmitter dopamine.

BACKGROUND OF THE INVENTION

Central nervous system (CNS) disorders are major public health issues. For example, Parkinson's disease (PD), the second most common neurodegenerative disease in the United States, affects over 1 million people while imposing an annual cost to the U.S. economy of 5.9 billion dollars. Clinically, PD is characterized by, among other signs, a decrease in spontaneous movements, gait difficulty, postural instability, rigidity, and tremor; these clinical signs are a direct result of the degeneration of the pigmented neurons (i.e., dopaminergic neurons) in the substantia nigra of the basal ganglia region of the brain. The progressive degeneration of the substantia nigra leads to decreased availability of dopamine, as the pigmented neurons of the substantia nigra are the sites of synthesis of this important catecholamine neurotransmitter.

Dopamine is synthesized in the terminal nerve endings of the dopaminergic neurons of the substantia nigra, specifically the substantia nigra pars compacta. The dopaminergic nerves project into the corpus striatum, specifically innervating the putamen and the caudate nucleus. Three enzymes are necessary for the efficient biosynthesis of dopamine: tyrosine hydroxylase (TH), guanosine triphosphate cyclohydrolase I (GCH), and aromatic L-amino acid decarboxylase (AADC). Tyrosine hydroxylase adds a hydroxyl group to the amino acid tyrosine creating L-dihydroxyphenylalanine (L-dopa). The enzymatic activity of TH requires the necessary cofactor tetrahydrobiopterin ($BH_4$), GCH catalyzing the first and rate-limiting step of the biosynthesis of $BH_4$. Lastly, AADC removes the terminal carboxyl group of L-dopa, which results in the formation of dopamine.

Currently, many CNS disorders such as PD are treated by systemic administration of a therapeutic agent. Systemic administration, however, can be ineffective because of a drug's inability to pass through the blood-brain-barrier and/or because of the potential for deleterious side effects. Thus, many potentially useful compounds, such as proteins, cannot be administered systemically. Treatment of PD currently involves oral administration of L-dopa, often in combination with a peripheral inhibitor of AADC. As PD progresses, a majority of patients experience a reduction in AADC content in affected regions of the brain (i.e., the substantia nigra). Since AADC converts L-dopa to dopamine, escalating doses of L-dopa are required for therapeutic efficacy, but this often results in increased side effects. Moreover, as the substantia nigra progressively deteriorates, AADC depletion continues unabated, often reaching a level where therapeutic benefit derived from administration of L-dopa is no longer realized.

In view of the limitations of current systemic therapies, gene delivery is a promising method for the treatment for CNS disorders such as PD. A number of viral based systems for gene transfer purposes have been described, including systems based on retroviruses and adenoviruses.

Adeno-associated virus (AAV) systems are emerging as the leading candidates for use in gene therapy. AAV is a helper-dependent DNA parvovirus that requires infection with an unrelated virus such as adenovirus, a herpesvirus or vaccinia, in order for a productive infection to occur. The helper virus supplies accessory functions that are necessary for most steps in AAV replication.

AAV infects a broad range of organisms as well as tissue types, without eliciting the cytotoxic effects and adverse immune reactions in animal models that have been observed with other viral vectors (see, e.g., Muzyczka, (1992) *Current Topics in Microbiol. and Immunol.* 158:97-129; Flotte et al. (1993) *Proc. Natl. Acad. Sci. USA* 90:10613-10617; Kasseiser et al. (1992) *Gene Therapy* 1:395-402; Yange et al. *Proc. Natl. Acad. Sci. USA* 91:4407-4411; Conrad et al. (1996) *Gene Therapy* 3:658-668; Yang et al. (1996) *Gene Therapy* 3:137-144; Brynes et al. (1996) *J. Neurosci.* 16:3045-3055). Because it can transduce non-dividing tissue, AAV may be well adapted for delivering genes to the central nervous system (CNS); indeed, AAV vectors containing therapeutic genes have been shown to transduce mammalian brain (see, e.g., During et al., (1998) *Gene Therapy* 5:820-827; Mandel et al. (1998) *J. Neurosci.* 18:4271-4284).

AAV vector delivery of dopamine-synthesizing enzymes to mammalian brain tissue has been described. Using a single gene approach, Kaplitt et al. (1994) *Nature Genetics* 8:148-153) stereotaxically injected recombinant AAV virions containing the gene coding for human tyrosine hydroxylase (rAAV-TH) to the denervated striatum of 6-hydroxydopamine (6-OHDA)-lesioned rats. Both neurons and glial cells were transduced. Delivery of rAAV-TH to monkey striatum resulted in expression of TH for up to 2.5 months (During et al., supra). Bankiewicz et al. demonstrated therapeutic levels of dopamine synthesis in 1-methyl-4-phenyl-1,2,3,6-tetrahydropyridine (MPTP)-treated monkeys after transduction of striatal cells with rAAV-AADC followed by oral administration of L-Dopa (Bankiewicz et al. (2000) *Exp Neurol* 164:2-14). Sanchez-Pemaute et al. demonstrated behavioral improvements in 6-OHDA-lesioned rats after transduction of striatal cells with rAAV-AADC (Sanchez-Pemaute et al. (2001) *Mol Ther* 4:324-330).

In a dual gene approach, Mandel et al., supra, co-transduced 6-OHDA-lesioned rats with AAV virions containing either TH or GCH genes (rAAV-TH and rAAV-GCH). Standard methods detected the presence of TH and GCH in the striatum of the 6-OHDA-lesioned rats. Similarly, in experiments described in During et al., supra, MPTP-treated green monkeys were co-transduced with rAAV-TH and rAAV virions containing the human AADC gene (rAAV-AADC). Gene expression was verified using standard techniques. Similarly, Fan et al. transduced 6-OHDA-lesioned rats after co-transduction of the striatum with rAAV-TH and rAAV-AADC virions (Fan et al. (1998) *Hum Gene Ther.* 9:2527-2535). Striatal levels of TH and AADC were measured using immunohistochemical staining. Rats expressing TH and AADC demonstrated increased behavioral recovery from 6-OHDA lesions than rats expressing TH or AADC alone.

Gene therapy for the treatment of PD has focused on transducing one or two dopamine biosynthetic enzymes into the CNS of animal models of PD. Under normal physiological conditions, efficient dopamine synthesis requires the presence of all three enzymes (Elsworth et al. (1997) *Exp. Neurol.* 144:4-9), which are anterogradely transported along the dopaminergic projections of the substantia nigra in the direction of the corpus striatum (for a detailed discussion see Nagatsu et al. (1990) Basic, Clinical, and Therapeutic Aspects of Alzheimer's and Parkinson's Disease. T. Nagatsu, A. Fisher, and M. Yoshida, eds. (Plenum Press, New York) pp. 263-266).

As discussed above, the dopaminergic neurons of the substantia nigra are depleted over time in patients with PD, greatly reducing dopamine synthesis and delivery to the corpus striatum; such a reduction culminates in the severe effects of advanced disease. By providing methods for the delivery and expression of all three enzymes in the corpus striatum of patients with PD, increased dopamine synthesis and hence increased therapeutic efficacy may be obtained. Such methods are disclosed herein.

SUMMARY OF THE INVENTION

The present invention describes methods of treating Parkinson's disease (PD) using recombinant adeno-associated virus (rAAV) virions comprising genes encoding enzymes in the dopamine biosynthetic pathway. In one embodiment, rAAV virions are provided which comprise three genes encoding enzymes in the dopamine biosynthetic pathway. Expression of these genes results in a therapeutic effect in a primate exhibiting symptoms associated with Parkinson's disease. Preferably, the primate is a human. Specifically, the genes comprise tyrosine hydroxylase (TH), aromatic amino L-acid decarboxylase (AADC), and guanosine triphosphate cyclohydrolase I (GCH).

The genes comprising dopamine biosynthetic enzymes are delivered to cells of the central nervous system (CNS) of a primate, preferably a human. In one embodiment cells of the corpus striatum are transduced by rAAV virions. In one aspect, cells of the putamen are transduced. In another aspect, cells of the caudate nucleus are transduced.

Delivery of rAAV virions is by way of surgical procedures. In one embodiment, delivery is by way of stereotaxis. In another embodiment, delivery is improved by way of using convection-enhanced delivery methods.

Once delivered, the genes are expressed in cells of the CNS resulting in a therapeutic effect to the primate exhibiting symptoms associated with PD. In one embodiment, the therapeutic effect is an increase in fine motor tasking. In a specific embodiment, the increase in fine motor tasking is an increase in manual dexterity. In another specific embodiment, the therapeutic effect is a reduction in resting tremor.

DETAILED DESCRIPTION OF THE INVENTION

Figure 1:
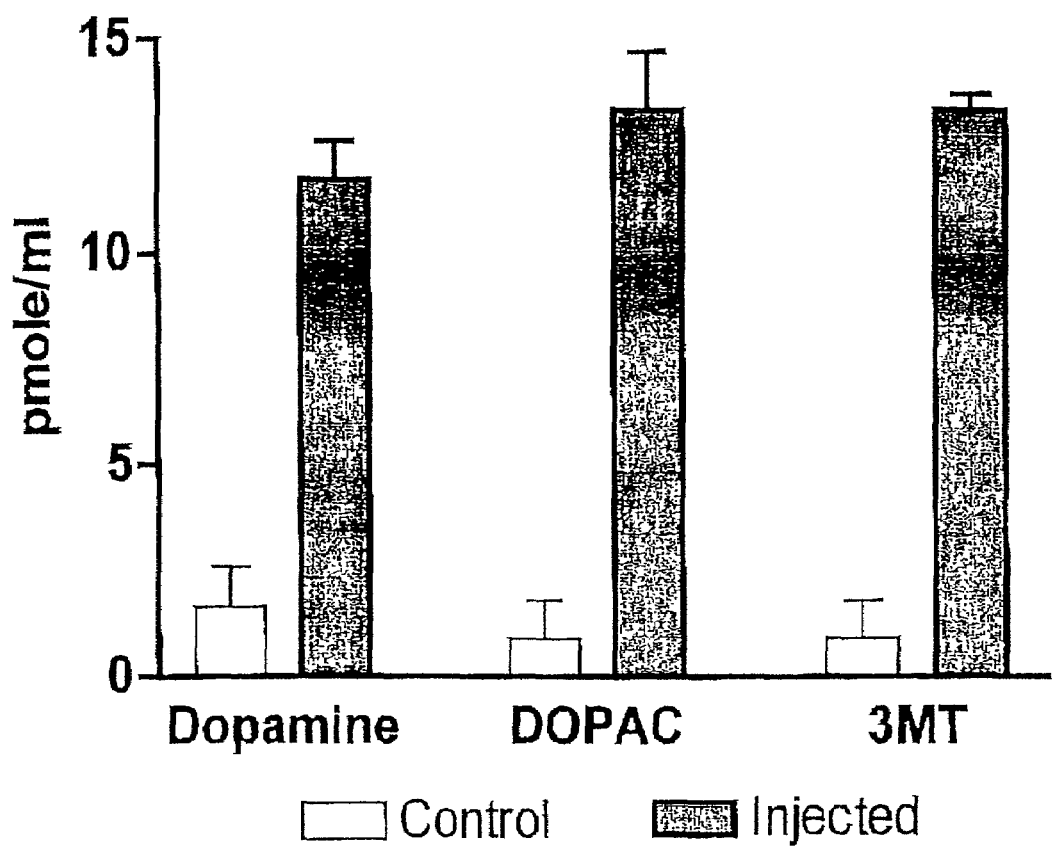
FIG. 1. In vivo synthesis of dopamine after striatal rAAV virion transductions. Dopamine and its metabolites, 3.4-dihydroxyphenylacetic acid (DOPAC) and 3-methoxytyramine (3MT), in the bilateral putamen were measured via microdialysis.

The present invention embraces the use of a recombinant adeno-associated virus (rAAV) virion to deliver a "heterologous gene" encoding one or more enzymes involved in the biosynthesis of dopamine to the brain of a mammalian subject. A "recombinant AAV virion" or "rAAV virion" is an infectious virus composed of an AAV protein shell (i.e., a capsid) encapsulating an "rAAV vector," the rAAV vector comprising the heterologous gene and one or more AAV inverted terminal repeats (ITRs). AAV vectors can be constructed using recombinant techniques that are known in the art and include one or more heterologous genes flanked by functional ITRs. The ITRs of the rAAV vector need not be the wild-type nucleotide sequences, and may be altered, e.g., by the insertion, deletion, or substitution of nucleotides, so long as the sequences provide for proper function, i.e., rescue, replication, and packaging of the AAV genome.

In the context of the present invention, a "recombinant AAV virion" or "rAAV virion" is an infectious virus composed of an AAV protein shell (i.e., a capsid) encapsulating a "recombinant AAV (rAAV) vector," the rAAV vector defined herein as comprising the HNA and one or more AAV inverted terminal repeats (ITRs). AAV vectors can be constructed using recombinant techniques that are known in the art and include one or more HNAs flanked by functional ITRs. The ITRs of the rAAV vector need not be the wild-type nucleotide sequences, and may be altered, e.g., by the insertion, deletion, or substitution of nucleotides, so long as the sequences provide for proper function, i.e., rescue, replication, and packaging of the AAV genome.

Recombinant AAV virions may be produced using a variety of techniques that are well known in the art. For example, the skilled artisan can use wt AAV and helper viruses to provide the necessary replicative functions for producing rAAV virions (see, e.g., U.S. Pat. No. 5,139,941, herein incorporated by reference). Alternatively, a plasmid, containing helper function genes, in combination with infection by one of the well-known helper viruses can be used as the source of replicative functions (see e.g., U.S. Pat. No. 5,622,856, herein incorporated by reference; U.S. Pat. No. 5,139,941, supra). Similarly, the skilled artisan can make use of a plasmid, containing accessory function genes, in combination with infection by wt AAV to provide the necessary replicative functions. As is familiar to one of skill in the art, these three approaches, when used in combination with a rAAV vector, are each sufficient to produce rAAV virions. Other approaches, well known to the skilled artisan, can be employed to produce rAAV virions.

In a preferred embodiment of the present invention, the triple transfection method (described in detail in U.S. Pat. No. 6,001,650, the entirety of which is incorporated by reference) is used to produce rAAV virions because this method does not require the use of an infectious helper virus, enabling rAAV virions to be produced without any detectable helper virus present. This is accomplished by use of three vectors for rAAV virion production: an AAV helper function vector, an accessory function vector, and a rAAV vector. One of skill in the art will appreciate, however, that the nucleic acid sequences encoded by these vectors can be provided on two or more vectors in various combinations. As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors.

The AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). An example of such a vector, pHLP19, is described in U.S. Pat. No. 6,001,650, the entirety of which is hereby incorporated by reference.

The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus. In a preferred embodiment, the accessory function plasmid pladeno5 is used (pLadeno5 is described in U.S. Pat. No. 6,004,797, the entirety of which is hereby incorporated by reference). This plasmid provides a complete set of adenovirus accessory functions for AAV vector production, but lacks the components necessary to form replication-competent adenovirus.

The "heterologous gene" comprises nucleic acid sequences joined together that are otherwise not found together in nature, this concept defining the term "heterologous." To illustrate the point, an example of a heterologous gene is one flanked by nucleotide sequences not found in association with that gene in nature. Another example of a heterologous gene is one that itself is not found in nature (e.g., synthetic sequences having codons different from the native gene). Allelic variation or naturally occurring mutational events do not give rise to heterologous genes, as used herein. In the context of the present invention, exemplary examples of heterologous genes are those that code for enzymes in the dopamine biosynthetic pathway, namely: aromatic L-amino acid decarboxylase, tyrosine hydroxylase, and guanosine triphosphate cyclohydrolase I.

The heterologous gene is operably linked to a heterologous promoter (constitutive, cell-specific, or inducible) such that the heterologous gene is capable of being expressed in the patient's target cells under appropriate or desirable conditions. Numerous examples of constitutive, cell-specific, and inducible promoters are known in the art, and one of skill could readily select a promoter for a specific intended use, e.g., the selection of the muscle-specific skeletal α-actin promoter or the muscle-specific creatine kinase promoter/enhancer for muscle cell-specific expression, the selection of the constitutive CMV promoter for strong levels of continuous or near-continuous expression, or the selection of the inducible ecdysone promoter for induced expression. Induced expression allows the skilled artisan to control the amount of protein that is synthesized. In this manner, it is possible to vary the concentration of therapeutic product. Other examples of well known inducible promoters are: steroid promoters (e.g., estrogen and androgen promoters) and metallothionein promoters.

It is often desirable to vary the concentration of a heterologous gene product in the host cell, for example, in order to achieve a "therapeutic effect." As described above, one way of accomplishing this is to make use of an inducible promoter. Alternatively, one of skill could vary the dose of rAAV virions. The dose of rAAV virions required to achieve a particular therapeutic effect, e.g., the units of dose in vector genomes/per kilogram of body weight (vg/kg), in turn, will vary based on several factors including, but not limited to: the route of rAAV virion administration, the level of heterologous gene expression required to achieve a therapeutic effect, and the stability of the heterologous gene product. One of skill in the art can readily determine a rAAV virion dose range to treat a patient having a particular disease or disorder based on the aforementioned factors, as well as other factors that are well known in the art.

Generally speaking, by "therapeutic effect" is meant a level of expression of one or more heterologous genes sufficient to alter a component of a disease (or disorder) toward a desired outcome or clinical endpoint, such that a patient's disease or disorder shows clinical improvement, often reflected by the amelioration of a clinical sign or symptom relating to the disease or disorder. In the case of Parkinson's disease, a therapeutic effect can be an improvement in motor function (e.g., fine motor tasking) manifested, for example, by improvement in manual dexterity. Alternatively, a reduction in resting tremor can also be a sign of amelioration of PD. There are several other art-recognized observable and measurable endpoints to determine therapeutic efficacy (i.e., a therapeutic effect) for a particular treatment of Parkinson's disease.

In human patients displaying clinical signs and symptoms of PD, clinicians often rely upon the well-known Unified Parkinson's Disease Rating Scale (UPDRS) to assess the severity of disease and also to measure the therapeutic efficacy of a particular treatment modality. Analogous to the UPDRS system, scientists assess PD features in primate models of Parkinsons's disease by using the Primate Parkinsonism Rating Scale (PPRS), which measures, among other features, fine motor tasking, resting tremor, bradykinesia, hypokinesia, and muscular rigidity. The PPRS system is described in Langston et al., (2000) *Ann Neurol* 47:S79-89.

Recombinant AAV virions are introduced into brain of a primate so that the TH, AADC, and GCH genes are expressed. Once these enzymes are expressed, dopamine is synthesized and made available to the appropriate functional areas of the basal ganglia. The replenishment of dopamine to the basal ganglia results in amelioration of the signs and symptoms associated with Parkinson's disease: such signs and symptoms include, but are not limited to, a decrease in spontaneous movements, gait difficulty, postural instability, rigidity, and tremor.

The basal ganglia are groups of neurons positioned subcortically. They include the caudate nucleus, putamen, and globus pallidus. The caudate nucleus and the putamen together form the corpus striatum (or simply striatum). The caudate and putamen are reciprocally interconnected with the substantia nigra, which consists of the substantia nigra pars compacta (SNpc) and the substantia nigra pars reticulata. The SNpc is the normal site of dopamine biosynthesis; degeneration of the SNpc is a hallmark of PD.

By transducing cells of the putamen or caudate nucleus of the corpus striatum with genes encoding enzymes in the dopamine biosynthetic pathway, dopamine synthesis can be restored, thereby overcoming a functionally diminished SNpc network.

Corpus striatal cells can be transduced using a variety of techniques known in the art. For example, stereotaxic injection is a common surgical technique used by neurosurgeons to administer various compounds to the CNS. Direct injection can also be employed; if using this technique, anatomical maps derived from CT, PET, or MRI scans can be used by the surgeon to aid in selecting the site or sites of injection. Other techniques, including convection-enhanced delivery (described in detail in U.S. Pat. No. 6,309,634, herein incorporated by reference in its entirety), can be employed in the methods of the present invention to deliver rAAV virions to the CNS.

The following examples are presented in order to more fully illustrate the preferred embodiments of the invention. They should in no way be construed, however, as limiting the broad scope of the invention.

EXAMPLE 1

Recombinant AAV Tyrosine Hydroxylase Virion Preparation

Recombinant AAV virions containing the human tyrosine hydroxylase type 1 (TH) gene—the complete cDNA sequence for TH available under GenBank Accession No. X05290—were prepared using a triple-transfection procedure described in U.S. Pat. No. 6,001,650, supra.

Vector Construction

AAV pHLP19 Helper Function Vector Construction

The AAV pHLP19 helper function vector was constructed using standard molecular biological techniques; its construction is described in detail in U.S. Pat. No. 6,001,650, supra.

To summarize, the AAV pHLP19 helper function vector was constructed in a several-step process using AAV-2 sequences derived from the AAV-2 provirus, pSM620, GenBank Accession Numbers K01624 and K01625. First, the ITRs were removed from the rep and cap sequences. Plasmid pSM620 was digested with SmaI and PvuII, and the 4543 bp rep- and cap-encoding SmaI fragment was cloned into the SmaI site of pUC19 to produce the 7705-bp plasmid, pUCrepcap. The remaining ITR sequence flanking the rep and cap genes was then deleted by oligonucleotide-directed mutagenesis using the oligonucleotides 145A (5'-GCTCGG-TACCCGGGCGGAGGGGTGGAGTCG-3') (SEQ ID NO 1) and 145B (5'-TAATCATTAACTACAGCCCGGGGATC-CTCT-3') (SEQ ID NO 2). The resulting plasmid, pUCRep-CapMutated (pUCRCM) (7559 bp) contains the entire AAV-2 genome (AAV-2 genome, GenBank Accession Number NC_001401) without any ITR sequence (4389 bp). SrfI sites, in part introduced by the mutagenic oligonucleotides, flank the rep and cap genes in this construct. The AAV sequences correspond to AAV-2 positions 146-4,534.

Second, an Eco47III restriction enzyme site was introduced at the 3' border of p5. This Eco47III site was introduced at the 3' end of the p5 promoter in order to facilitate excision of the p5 promoter sequences. To do this, pUCRCM was mutagenized with primer P547 (5'-GGTTTGAAC-GAGCGCTCGCCATGC-3') (SEQ ID NO 3). The resulting 7559 bp plasmid was called pUCRCM47III.

Third, an assembly plasmid, called pBluntscript, was constructed. The polylinker of pBSII SK+ was changed by excision of the original with BssHII and replaced with oligonucleotides blunt 1 and 2. The resulting plasmid, pBluntscript, is 2830 bp in length, and the new polylinker encodes the restriction sites EcoRV, HpaI, SrfI, PmeI, and Eco47III. The blunt 1 sequence is 5'-CGCGCCGATATCGTTAACGC-CCGGGCGTTTAAACAGCGCTGG-3' (SEQ ID NO 4) and the blunt 2 sequence is 5'-CGCGCCAGCGCTGTT-TAAACGCCCGGGCGTTAACGATATCGG-3' (SEQ ID NO 5).

Fourth, the plasmid pH1 was constructed by ligating the 4397 bp rep- and cap-encoding SmaI fragment from pUCRCM into the SrfI site of pBluntscript, such that the HpaI site was proximal to the rep gene. Plasmid pH1 is 7228 bp in length.

Fifth, the plasmid pH2 was constructed. Plasmid pH2 is identical to pH1 except that the p5 promoter of pH1 was replaced by the 5' untranslated region of pGN1909 (ATCC Accession Number 69871. Plasmid pGN1909 construction is described in detail in U.S. Pat. No. 5,622,856, herein incorporated by reference in its entirety). To accomplish this, the 329 bp AscI(blunt)-SfiI fragment encoding the 5' untranslated region from pW1909lacZ (described in detail in U.S. Pat. No. 5,622,856, supra) was ligated into the 6831 bp SmaI(partial)-SfiI fragment of pH1, creating pH2. Plasmid pH2 is 7155 bp in length.

Sixth, pH8 was constructed. A p5 promoter was added to the 3' end of pH2 by insertion of the 172 bp, SmaI-Eco47III fragment encoding the p5 promoter from pUCRCM47III into the Eco47III site in pH2. This fragment was oriented such that the direction of transcription of all three AAV promoters are the same. This construct is 7327 bp in length.

Seventh, the AAV helper function vector pHLP19 was constructed. The TATA box of the 3' p5 (AAV-2 positions 255-261, sequence TATTTAA (SEQ ID NO 6)) was eliminated by changing the sequence to GGGGGGG (SEQ ID NO 7) using the mutagenic oligonucleotide 5DIVE2 (5'-TGTG-GTCACGCTGGGGGGGGGGGCCCGAGTGAGCACG-3') (SEQ ID NO 8). The resulting construct, pHLP19, is 7327 bp in length.

pLadeno1 Accessory Function Vector Construction

The pLadeno1, accessory function vector is described in detail in U.S. Pat. No. 6,004,797, herein incorporated by reference in its entirety. To summarize, pLadeno1 containing adenovirus VA RNA, E4 and E2a gene regions, was assembled by cloning adenovirus type-5 genes into a custom polylinker that was inserted between the PvuII sites of pBSII s/k-. More particularly, a double stranded oligonucleotide polylinker encoding the restriction enzyme sites SalI-XbaI-EcoRV-SrfI-BamHI (5'-GTCGACAAATCTAGATATCGC-CCGGGCGGATCC-3') (SEQ ID NO 9) was ligated to the 2513 bp PvuII vector fragment of pBSII s/k- to provide an assembly plasmid. The following fragments containing adenovirus type-5 genes or gene regions were then obtained from the pJM17 plasmid (the pJM17 plasmid described in detail in McGrory et al. (1988) *Virology* 163:614-617): the 1,724 bp SalI-HinDIII VA RNA-containing fragment (corresponding to the nucleotides spanning positions about 9,831 to about 11,555 of the adenovirus type-2 genome—the complete adenovirus type-2 genome available under GenBank Accession Number NC_001405); the 5,962 bp SrfI-BamHI E2a-containing fragment (corresponding to the nucleotides spanning positions about 21,606 to about 27,568 of the adenovirus type-2 genome); and the 3,669 bp HphI-HinDIII E4-containing fragment (corresponding to the nucleotides spanning positions about 32,172 to about 36,841 of the adenovirus type-2 genome). An XbaI site was added to the HphI end of the E4-containing fragment by cloning the 3,669 bp HphI-HinDIII fragment into the HpaI site of cloning vector, and then excising the fragment with XbaI and HinDIII (partial digestion). The 5,962 E2a-containing fragment was cloned between the SrfI and BamHI sites of the assembly plasmid, and the 1,724 bp VA RNA-containing fragment and the modified 3,669 bp E4-containing fragments were joined by their common HinDIII ends and ligated between the SalL and XbaI sites of the assembly plasmid to obtain the pLadeno1 construct.

Recombinant AAV-TH Vector Construction

The recombinant AAV-TH vector was constructed from a parent plasmid containing the lacZ gene. The parent plasmid was constructed as follows: A 2.7-kb KasI-EarI fragment from pUC119 (GenBank Accession Number U07650) was blunted and ligated to a multiple cloning sequence containing the following restriction enzyme sites (5'-NotI-MluI-SnaBI-AgeI-BstBI-BssHII-NcoI-HpaI-BspEI-PmlI-RsrII-NotI-3'). The following fragments were successively cloned into the SnaBI site, a BstBI-BstBI fragment from the human growth hormone first intron was inserted into the BstBI site, the lacZ gene was ligated into the BssHII site, and HpaI-BamHI fragment of the simian virus 40 (SV40) polyadenylation signal sequence was cloned into the HpaI site. The resulting NotI-NotI expression cassette was inserted between the AAV 145-bp inverted terminal repeats of a pUC-based plasmid. The pTH vector plasmid was constructed by excising the lacZ gene from the parent vector plasmid and replacing it with the 1.8-kb human TH (type 1) gene (GenBank Accession No. X05290).

Recombinant AAV-TH Virion Production

Recombinant AAV-TH virions were produced using a triple transfection method described in U.S. Pat. Nos. 6,001,650 and 6,004,797, supra. To summarize, cells from the stable human cell line, 293 (readily available through, e.g., ATCC under Accession Number CRL1573), were plated in eight 10-cm tissue culture dishes at $1 \times 10^6$ cells at 37° C. to reach 90% confluency over a period of from about 24 to 48 hours prior to transfection.

Transfections were carried out using the calcium phosphate method. Specifically, at 1 to 4 hours prior to transfection, the medium in the tissue culture plates was replaced with fresh Dulbeco's Modified Eagles Medium (DMEM)/F12 (GIBCO, BRL) containing 10% fetal calf serum, 1% penicillin/streptomycin, and 1% glutamine. A total of 10 µg each of DNA from the three vectors, pHLP19, pLadeno1, and rAAV-TH were added to 1 mL of sterile 300 mM $CaCl_2$, which was then added to 1 mL of sterile 2×HBS solution (formed by mixing 280 mM NaCl, 50 mM HEPES buffer, 1.5 mM $Na_2HPO_4$ and adjusting the pH to 7.1 with 10 M NaOH) and immediately mixed by gentle inversion. The resultant mixture was pipetted immediately into the 10 cm plates of 90% confluent 293 cells (in 10 mL of the above-described culture medium) and swirled to produce a homogeneous solution. The plates were transferred to a 5% $CO_2$ incubator and cultured at 37° C. for approximately 5 hours without disturbing. After transfection, the medium was removed from the plates, and the cells washed once with sterile Phosphate buffered saline (PBS). New culture medium was added and the cells were incubated at 37° C. for approximately 72 hours.

The cells were then collected, media was removed by centrifugation (1000×g for 10 min.), and a 1 mL lysate (cells lysed in Tris buffer—10 mM Tris 150 mM NaCl, pH8.0) was produced using 3 freeze/thaw cycles (alternating between dry ice-ethanol and 37° C. water baths). The lysates were made free of debris by centrifugation (12,000×g for 10 min).

Recombinant AAV-TH virions were then purified by two sequential continuous cesium chloridate gradient ultracentrifugations. Recombinant AAV-TH titer was determined by quantitative dot-blot hybridization of DNAseI-treated recombinant AAV-TH stocks.

EXAMPLE 2

Recombinant AAV Aromatic Amino Acid Decarboxylase Virion Preparation

Recombinant AAV virions containing the human aromatic L-amino acid decarboxylase (AADC) gene—the complete cDNA sequence for AADC available under GenBank Accession No. M76180—were prepared using a triple-transfection procedure described in U.S. Pat. No. 6,001,650, supra. In summary the AAV pHLP19 helper function vector, the pLadeno1 accessory function vector, and the rAAV-AADC vector were used to produce rAAV-AADC virions.

The AAV pHLP19 helper function vector and the pLadeno1 accessory function vector were constructed as described in Example 1.

Recombinant AAV-AADC Vector Construction

The recombinant AAV-AADC vector was constructed exactly as in Example 1 for rAAV-TH vector production, with the exception that the AADC gene (GenBank Accession No. M76180) was used.

Recombinant AAV-AADC Virion Production

Recombinant AAV-AADC virion production was accomplished exactly as described in Example 1 for rAAV-TH virion production with the exception that the rAAV-AADC vector was used instead of the rAAV-TH vector.

EXAMPLE 3

Recombinant AAV Guanosine Triphosphate Cyclohydrolase I Virion Preparation

Recombinant AAV virions containing the human guanosine triphosphate cyclohydrolase I (GCH) gene—the complete cDNA sequence for GCH available under GenBank Accession No. NM_000161—were prepared using a triple-transfection procedure described in U.S. Pat. No. 6,001,650, supra. In summary, the AAV pHLP19 helper function vector and the pLadeno1 accessory function vector and the rAAV-GCH vector were used to produce rAAV-GCH virions.

The AAV pHLP19 helper function vector and the pLadeno1 accessory function vector were constructed as described in Example 1.

Recombinant AAV-GCH Vector Construction

The recombinant AAV-GCH vector was constructed exactly as in Example 1 for rAAV-TH vector production, with the exception that the GCH gene (GenBank Accession No. NM_000161) was used.

Recombinant AAV-GCH Virion Production

Recombinant AAV-GCH virion production was accomplished exactly as described in Example 1 for rAAV-TH virion production with the exception that the rAAV-GCH vector was used instead of the rAAV-TH vector.

EXAMPLE 4

1-METHYL-4-PHENYL-1,2,3,6-TETRAHYDROPYRIDINE Treatment OF Cynomolgus Macaques Four female cynomolgus macaques (*Macaca fascicularis*) designated M-1, M-2, M-3, and M-4, each weighing between 2 and 2.5 kg, served as the experimental subjects. Two of the four macaques, M-1 and M-2 had been trained to perform fine motor tasks such as capturing four raisins or small pieces of apple with each of the two hands. To make bilateral striatal lesions, MPTP-HCl (0.25 to 0.5 mg/kg of free base; Sigma, St. Louis, Mo.) in PBS was injected intravenously once a week until a stable parkinsonian syndrome was achieved. The total doses of MPTP were 1.0 to 6.25 mg/kg for seven consecutive months. To avoid the possibility that spontaneous recovery from acute toxicity to MPTP could resemble the behavioral effects of AAV injection, macaques were allowed to recover for two months after the last MPTP treatment.

EXAMPLE 5

Surgery and Recombinant AAV Virion Injection

Surgery on the macaques was performed under general anesthesia (1-2% isoflurane). The head was placed in a stereotactic device (Kopf Instruments, Tujunga, Calif.) for the procedure. Each macaque received nine injections of AAV virions in three tracts in the unilateral putamen. The side of injection was randomly assigned (the right side for macaque M-1, the left for M-2, M-3, and M-4). Each AAV injection consisted of 5 µL with a 1:1:1 mixture of rAAV-TH, rAAV-AADC, and rAAV-GCH (at a concentration of $1 \times 10^{13}$ virion particles per mL for each vector type, i.e., $1 \times 10^{13}$ rAAV-TH virions, $1 \times 10^{13}$ rAAV-AADC virions, and $1 \times 10^{13}$ rAAV-GCH virions). Injections were made through a Hamilton microsyringe at a rate of 1 µL/min. The needle was left in place for an additional five minutes to prevent the loss of virions by back flow. As a control, 15 µL of rAAV-LacZ ($1 \times 10^{13}$ virion particles per mL, in macaque M-1) or PBS (in macaque M-2, M-3, and M-4) was injected into the contralateral putamen.

EXAMPLE 6

Microdialysis and High Performance Liquid Chromatography

Figure 2:
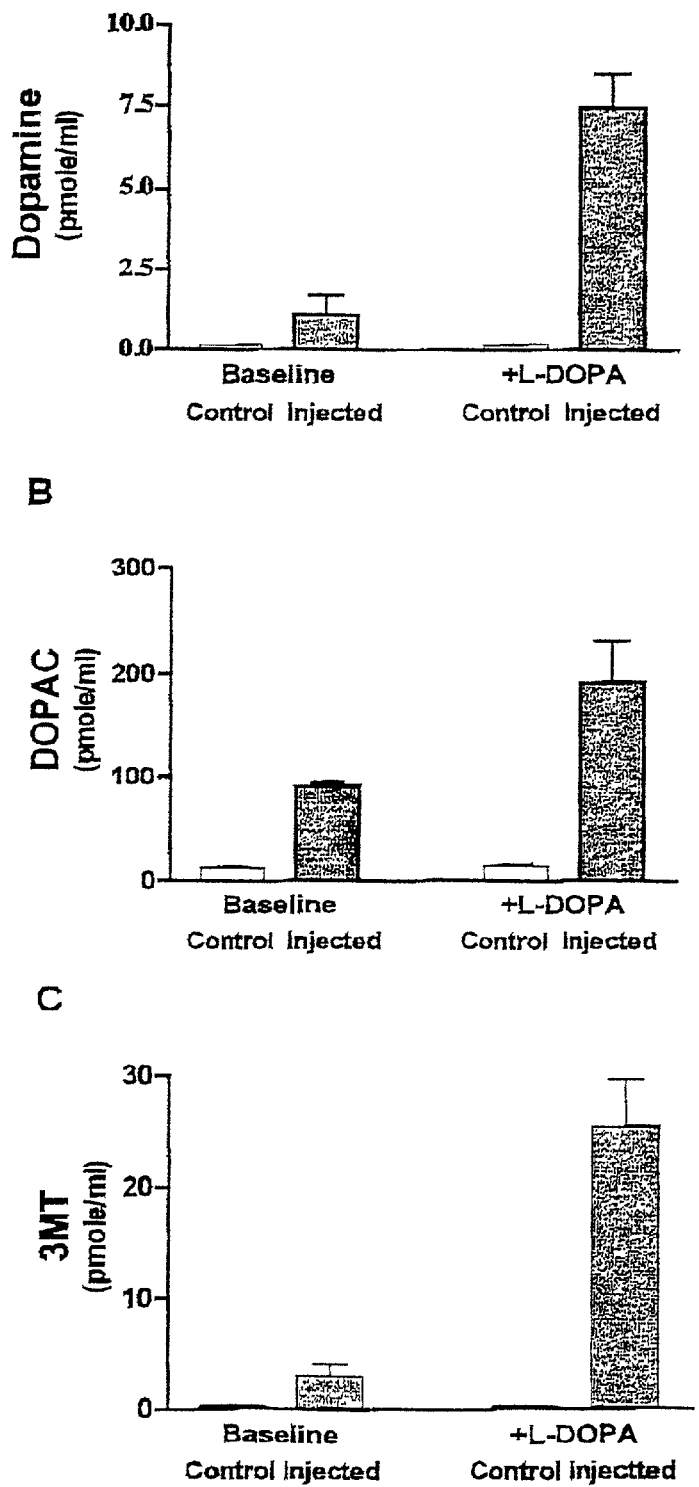
FIG. 2. Enhancement of in vivo dopamine synthesis after systemic administration of L-dihydroxyphenylalanine (L-dopa) and peripheral AADC inhibitor. (a) dopamine (b) DOPAC (c) 3MT levels were elevated in the rAAV-TH/-AADC/-GCH-treated putamen of an MPTP-treated monkey.

To determine dopamine, DOPAC, and 3MT concentration in rAAV-injected macaques, microdialysis experiments were performed in macaques M-2 and M-3. The dialysis probes used were the concentric type (0.22 mm diameter) and had 10 mm of exposed dialysis membrane (Eicom, Kyoto, Japan). The probes were implanted in the putamen bilaterally and Ringer's solution was passed through them at a rate of 10 µM/min for 20 min to remove dopamine overflow from the damaged tissue. The perfusion rate was decreased to 2 µL/min and maintained during the experiment. Two hours after the insertion of the probes, 30 µL of samples were collected every 15 min for 60 min (four samples collected). To study the effect of systemic administration of L-Dopa, 50 mg/kg of L-Dopa, and 5 mg/kg of carbidopa were injected i.v. followed by a 50 mg/kg L-Dopa d.i.v. after the baseline samples were determined by high performance liquid chromatography with electrochemical detection using an Eikompak MA-50ODS column (Eicom, Kyoto, Japan). The minimum detection limit for dopamine was 1 nM. As FIGS. 1 and 2 show, significant concentrations of dopamine formation and significant increases in the concentration of dopamine metabolites DOPAC and 3MT were observed in rAAV-TH/-AADC/-GCH macaques, indicating robust dopamine synthesis in the treated macaques relative to the untreated (control) macaques.

EXAMPLE 7

Behavioral Assessment of MPTP-Treated Cynomolgus Macaques

MPTP-treated macaques were clinically evaluated twice a week using the PPRS method. The PPRS scores independently from 0 (normal) to 4 (maximal disability). Macaques were evaluated for six parkinsonian features: spatial hypokinesia, bradykinesia, manual dexterity of right arm, manual dexterity of left arm, balance, and freezing, thus giving a maximum score of 24. Disability scores are given in Table 1 and consist of average values of the six evaluations conducted three weeks prior to AAV injection (Before AAV injection column) and three weeks prior to sacrifice (After AAV injection column). As Table 1 indicates, each rAAV-treated macaque showed significant improvement in its PPRS scores. In two macaques, M-2 and M-3, a 66% improvement was observed in their PPRS scores. Macaque M-1 showed a 61% improvement in its PPRS score whereas M-4, while showing strong improvement, had an overall reduction in PPRS score of 30%.

Hand movements on the fine motor tasks were analyzed by counting the pixels of digital recordings using an image subtraction method described in Hashimoto et al. (1999) *J Neurosci Methods* 91:115-122. To summarize, a video camera was situated in front of a tray on which four raisins were placed in line from backward (macaque side) to forward (observer side). While macaques sequentially picked up four raisins, the numbers of pixels representing the hand were increased when the hand was coming forward to reach each raisin. Time spent on picking up each raisin was measured before and after the AAV injection. Results for the ipsilateral and contralateral hands are given in Table 1. As Table 1 indicates, the time span for picking up raisins in the contralateral hand (the "treated" hand, i.e., the hand affected by rAAV injection into the unilateral putamen) decreased to the normal range (<0.3 sec per motion), whereas the ipsilateral hand (i.e., "untreated" hand) did not show a decrease in time span for picking up raisins.

EXAMPLE 8

Immunohistochemistry

Under deep anesthesia, each macaque was perfused through the ascending aorta with 0.01 M PBS, followed by 4% paraformaldehyde. The brains were removed and cut into several blocks 5 mm thick. The tissue blocks were post-fixed in the same fixative, followed by a rinse for 3 days in PBS containing 15% sucrose. The blocks were cut into coronal sections 30 µM thick on a cryostat. The sections were then treated with 40% methanol and 1% H2O2 for 20 min to inhibit endogenous peroxidase. The sections were incubated in primary antibodies against TH or AADC diluted 1:10000, or GCH diluted to 1:8000 in PBS containing 0.3% Triton X-100 at 4° C. for two days. Then they were incubated in biotinylated rabbit IgG (Vector Laboratory; 1:1000 dilution) for 2 h at 4° C., and then avidin-biotin peroxidase complex (Vector Laboratory: 1:1000 dilution) for 1 h at room temperature. Peroxidase activity was revealed in 50 mM Tris-HCl buffer (pH7.6) containing 0.0003% $H_2O_2$, 0.01% 3.3'-diaminobenzidine-4HCl (DAB) and 1% nickel ammonium sulfate. Normal macaque brain slices were used as a control. For dual immunofluorescence staining for MAP-2 and TH, sections were incubated with a mixture of mouse monoclonal anti-MAP-2 antibody (1:500; Sigma, St. Louis, Mo.) and rabbit polyclonal anti-TH antibody (1:500) followed by incubation with Alexa Fluor 448-conjugated goat anti-mouse IgG (2 μg/mL; Molecular Probes, Inc.) and Alexa Fluor 594-conjugated goat anti-rabbit IgG (2 μg/mL; Molecular Probes, Inc.). Immunoreactivity was examined and viewed with a confocal laser-scanning microscope (TCT NT; Leica, Germany). Immunohistochemical staining revealed that nearly all of the cells that stained positive were neurons, with the vast majority displaying morphological features of medium spiny neurons.

TABLE 1

BEHAVIORAL RECOVERY OF MPTP-TREATED MACAQUES AFTER AAV VIRION INJECTIONS

| Macaque | PPRS[1] | | Fine Motor Tasking[2] | |
|---|---|---|---|---|
| | Before AAV Injection | After AAV Injection | Ipsilateral Hand | Contralateral Hand |
| M-1 | 17.2 ± 0.17 | 6.8 ± 0.16 | 0.71 ± 0.17 | 0.20 ± 0.04 |
| M-2 | 18.7 ± 0.21 | 6.3 ± 0.21 | 0.58 ± 0.19 | 0.23 ± 0.04 |
| M-3 | 18.8 ± 0.17 | 6.5 ± 0.22 | ND[3] | ND |
| M-4 | 23.7 ± 0.21 | 16.5 ± 0.22 | ND | ND |

[1]Average (mean ± SEM) of six evaluation sessions.
[2]Picking up time (seconds; mean ± SEM) of raisins from eight trials after rAAV-TH/-AADC/-GCH injection into the unilateral putamen.
[3]Not Done.

We claim:

1. A method of treating Parkinson's disease in a primate, comprising:
   a) providing recombinant adeno-associated virus (rAAV) virions comprising heterologous genes encoding dopamine synthesizing enzymes wherein said dopamine synthesizing enzymes comprise tyrosine hydroxylase, aromatic L-amino acid decarboxylase, and guanosine triphosphate cyclohydrolase I;
   b) injecting into the striatum of said primate said rAAV virions wherein at least one corpus striatal cell of said primate is transduced; and
   c) expressing said heterologous genes wherein expression results in a therapeutic effect in said primate, and wherein said therapeutic effect in said primate is an improvement in fine motor tasking.

2. A method of treating Parkinson's disease in a primate comprising:
   a) providing recombinant adeno-associated virus (rAAV) virions comprising heterologous genes encoding dopamine synthesizing enzymes wherein said dopamine synthesizing enzymes comprise tyrosine hydroxylase, aromatic L-amino acid decarboxylase, and guanosine triphosphate cyclohydrolase I;
   b) injecting into the striatum of said primate said rAAV virions wherein at least one corpus striatal cell of said primate is transduced; and
   c) expressing said heterologous genes wherein expression results in a therapeutic effect in said primate, and wherein said therapeutic effect in said primate is an improvement in manual dexterity.

3. A method of treating Parkinson's disease in a primate, comprising:

a) providing recombinant adeno-associated virus (rAAV) virions comprising heterologous genes encoding dopamine synthesizing enzymes wherein said dopamine synthesizing enzymes comprise tyrosine hydroxylase, aromatic L-amino acid decarboxylase, and guanosine triphosphate cyclohydrolase I;

b) injecting into the striatum of said primate said rAAV virions wherein at least one corpus striatal cell of said primate is transduced; and c) expressing said heterologous genes wherein expression results in a therapeutic effect in said primate, and wherein said therapeutic effect in said primate is a reduction in resting tremor.

* * * * *